United States Patent
Barklett-Judge

(10) Patent No.: US 12,168,032 B2
(45) Date of Patent: Dec. 17, 2024

(54) CALMING COMPOSITION

(71) Applicant: PET REMEDY LIMITED, Devon (GB)

(72) Inventor: Martyn Christopher Barklett-Judge, Torquay (GB)

(73) Assignee: PET REMEDY LIMITED (GB)

( * ) Notice: Subject to any disclaimer, the term of this patent is extended or adjusted under 35 U.S.C. 154(b) by 1134 days.

(21) Appl. No.: 16/979,579

(22) PCT Filed: Mar. 8, 2019

(86) PCT No.: PCT/GB2019/050656
§ 371 (c)(1),
(2) Date: Sep. 10, 2020

(87) PCT Pub. No.: WO2019/175550
PCT Pub. Date: Sep. 19, 2019

(65) Prior Publication Data
US 2021/0000903 A1  Jan. 7, 2021

(30) Foreign Application Priority Data
Mar. 12, 2018 (GB) ..................... 1803946

(51) Int. Cl.
| | | |
|---|---|---|
| *A61K 36/84* | (2006.01) | |
| *A61K 9/00* | (2006.01) | |
| *A61K 9/107* | (2006.01) | |
| *A61K 36/53* | (2006.01) | |
| *A61K 36/537* | (2006.01) | |
| *A61K 36/899* | (2006.01) | |
| *A61K 47/02* | (2006.01) | |
| *A61K 47/18* | (2017.01) | |
| *A61K 47/22* | (2006.01) | |
| *A61K 47/26* | (2006.01) | |
| *A61M 11/00* | (2006.01) | |
| *A61P 25/20* | (2006.01) | |

(52) U.S. Cl.
CPC ............ *A61K 36/84* (2013.01); *A61K 9/0073* (2013.01); *A61K 9/107* (2013.01); *A61K 36/53* (2013.01); *A61K 36/537* (2013.01); *A61K 36/899* (2013.01); *A61K 47/02* (2013.01); *A61K 47/183* (2013.01); *A61K 47/22* (2013.01); *A61K 47/26* (2013.01); *A61M 11/007* (2014.02); *A61P 25/20* (2018.01); *A61K 2236/30* (2013.01)

(58) Field of Classification Search
None
See application file for complete search history.

(56) References Cited

U.S. PATENT DOCUMENTS

2003/0054049 A1* 3/2003 Shoji ................... A61K 8/922
424/733
2015/0342854 A1* 12/2015 Shibuya ............. A61K 8/9761
424/769

FOREIGN PATENT DOCUMENTS

| GB | 2474042 | | 4/2011 | | |
|---|---|---|---|---|---|
| GB | 2474042 | A * | 4/2011 | ............. | A61K 36/53 |
| WO | WO 00/37092 | | 6/2000 | | |
| WO | WO-2015110800 | A1 * | 7/2015 | ............. | A01N 65/00 |

OTHER PUBLICATIONS

Database WPI Week 201617, Thomson Scientific, London, GB AN 2015-73502G, XP002790793, & CN104983927, Oct. 21, 2015, 1 page.
Database WPI Week 201749, Thomson Scientific, London, GB; AN 2017-43117E, XP002790794, & CN106729068, May 31, 2017, 2 pages.
Database WPI Week 201712, Thomson Scientific, London, GB; AN 2016-729138, XP002790795, & CN106118884, Nov. 16, 2016, 2 pages.
Database WPI Week 201681, Thomson Scientific, London, GB; AN 2016-59235M, XP002790796, & CN105902854, Aug. 31, 2016, 2 pages.
"Pet Remedy Natural De-Stress and Calming Refill Pack, 40 ml, Pack of 2," Amazon.com, Inc., First Available Aug. 8, 2009, 10 pages [retrieved online from: www.amazon.co.uk/Pet-Remedy-Natural-Stress-Refill/dp/B006H2UDW0].
Taylor et al. "The effect of Pet Remedy on the Behaviour of the Domestic Dog (Canis familiaris)," Animals, 2016, vol. 6, No. 11, , Article 64, 9 pages.
Search Report for United Kingdom Patent Application No. GB1803946.1, dated Oct. 15, 2018, 6 pages.
International Search Report and Written Opinion for International (PCT) Patent Application No. PCT/GB2019/050656, dated May 6, 2019, 15 pages.
International Preliminary Report on Patentability for International (PCT) Patent Application No. PCT/GB2019/050656, dated Sep. 24, 2020, 9 pages.

* cited by examiner

*Primary Examiner* — Robert A Wax
*Assistant Examiner* — Quanglong N Truong
(74) *Attorney, Agent, or Firm* — Sheridan Ross PC

(57) ABSTRACT

Certain embodiments of the present invention relate to compositions for calming and de-stressing animals. In particular, but not exclusively, certain embodiments of the present invention relate to compositions comprising valerian oil.

20 Claims, 4 Drawing Sheets

CALMING COMPOSITION

CROSS REFERENCE TO RELATED APPLICATIONS

This application is a national stage application under 35 U.S.C. 371 and claims the benefit of PCT Application No. PCT/GB2019/050656 having an international filing date of 8 Mar. 2019, which designated the United States, and which PCT application claimed the benefit of Great Britain Patent Application No. 1803946.1 filed 12 Mar. 2018, the contents of each of which are incorporated herein by reference in their entireties.

FIELD OF INVENTION

Certain embodiments of the present invention relate to compositions for calming and destressing animals. In particular, but not exclusively, certain embodiments of the present invention relate to compositions comprising valerian oil.

BACKGROUND

Stress and anxiety is becoming a more prevalent problem for animals and humans. Stress can be caused by a number of different environmental and social factors. For both humans and animals changes in their environment, routine or certain social interactions can cause stress and anxiety.

One solution known in the prior art to help reduce the symptoms of stress and calm an animal or human has been the use of pheromone containing compositions but evidence of efficacy of such compositions has yet to be proven. A further disadvantage of pheromone containing compositions is that pheromones are often species specific and therefore do not provide a composition that can be used for a range of species.

Another prior art solution for use in both humans and animals is the use of pharmaceuticals such as sedatives or tranquilizers. These can be difficult to administer to animals, may require a relatively long period of time to take effect and may interfere or not be suitable for animals or humans with pre-existing medical conditions or taking certain other medications. They may also cause a number of adverse side effects. These may also over sedate an animal or human meaning they may become unresponsive or lethargic rather than reducing the symptoms of stress.

The use of compositions of absolute and essential oils for helping to relieve stress, the symptoms of stress and anxiety is known. These compositions suffer from the disadvantage that they have a delay between delivery and exhibiting effect in a target animal or human. Prior art compositions may also lead to sedation of an animal or human which for both humans and animals can lead to a lack of responsiveness and attentiveness.

A disadvantage associated with many prior art compositions and treatments, whether pheromone based, or essential oil based, is that they often utilise synthetic components or synthetic analogues which may have undesirable off target side effects as well as producing compositions that may be damaging to the environment when applied or when disposed of. Often valerian oils used in many preparations are quite potent and concentrated and therefore more sedating than calming. The advantage with a water based, low concentration and pH neutral formulation is that it is very gentle and more suitable for use on skin and coat of animal.

It is an aim of the present invention to at least partly mitigate the above-mentioned problems.

It is an aim of certain embodiments of the present invention to provide a composition for reducing the symptoms of stress of an animal or human that does not sedate the animal or human.

It is an aim of certain embodiments of the present invention to provide a composition for calming and destressing an animal or human which has improved properties.

It is an aim of certain embodiments of the present invention to provide a composition for reducing the symptoms of stress of an animal or human that is fast acting.

It is an aim of certain embodiments of the present invention to provide a composition for reducing the symptoms of stress of an animal or human that has a prolonged effect.

It is an aim of certain embodiments of the present invention to provide a composition for reducing the symptoms of stress of an animal or human that is environmentally friendly.

It is an aim of certain embodiments of the present invention to provide a composition that has a stabilised pH when stored and used over a period of time.

SUMMARY OF INVENTION

According to a first aspect of the present invention there is provided, a composition for reducing the symptoms of stress of an animal or human, the composition comprising:
   a.) valerian oil;
   b.) one or more further essential oils;
   c.) water;
   d.) at least one preservative;
   e.) at least one solvent;
   f.) at least one pH stabiliser; and
   g.) at least one emulsifier.

In certain embodiments, the composition comprises valerian oil in an amount of between about 0.01% to about 1% volume per volume (v/v) of the composition. Aptly, the composition comprises valerian oil in an amount of between about 0.05% to about 0.5% v/v of the composition. Aptly, the composition comprises valerian oil in an amount of between about 0.1% to about 0.3% v/v. For example, in one embodiment, the composition comprises valerian oil in an amount of about 0.27% v/v of the composition. In another embodiment, the composition comprises valerian oil in an amount of about 0.1% v/v of the composition.

In certain embodiments, the composition comprises water in an amount of at least about 79% v/v of the composition. Aptly, the composition comprises water in an amount of at least about 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% v/v of the composition. For example, in one embodiment, the composition comprises water in an amount of about 89% v/v of the composition.

Aptly, the water is purified water.

In certain embodiments, the one or more further essential oils comprises one or more of vetiver and/or basil and/or sage. Aptly, the one or more essential oils is a mixture of vetiver, basil and sage. In certain embodiments, the one or more further essential oils provide an aroma to the composition as well as enhancing the calming and destressing effects of the composition.

Aptly, the sage oil is clary sage oil.

In certain embodiments, the composition comprises one or more essential oils in a total amount of between about 0.01% to about 1% v/v of the composition. Aptly, the composition comprises one or more essential oils in a total amount of between about 0.05% and about 0.5% v/v of the composition. Aptly, the composition comprises one or more essential oils in a total amount of between about 0.1% and about 0.4% v/v of the composition. For example, in one embodiment, the composition comprises one or more essential oils in a total amount of about 0.4% v/v of the composition. In one embodiment, the composition comprises one or more essential oils in a total amount of about 0.3% v/v of the composition. In certain embodiments, the percentage of volume per volume of further essential oils in the composition is the cumulative percentage of each further essential oil in the composition. For example, in one embodiment, the composition comprises 0.1% v/v basil essential oil, 0.1% v/v clary sage essential oil and 0.2% v/v vetiver essential oil, thus giving a total percentage of the one or more essential oils of 0.4% v/v of the composition.

In certain embodiments, the composition comprises the at least one emulsifier in an amount of between about 1% and 9% v/v of the composition. Aptly, the composition comprises the at least one emulsifier in an amount of between about 2% v/v and 7% v/v, e.g. between about 4% and 6% v/v and for example 5% v/v of the composition.

In certain embodiments, the at least one emulsifier comprises at least one surfactant. Aptly, the at least one surfactant comprises at least one ethoxylated sorbitan ester. Aptly, the at least one ethoxylated sorbitan ester comprises polyoxyethelyene sorbitan monolaurate.

In certain embodiments, the composition comprises the at least one solvent in an amount of between about 1% and 9% v/v of the composition. Aptly, the composition comprises the at least one solvent in an amount of between about 3% to 7% v/v of the composition. Aptly, the composition comprises the at least one solvent in an amount of between about 4% and 6% v/v of the composition. For example, 5% v/v.

In certain embodiments, the at least on solvent comprises a low odour solvent.

In certain embodiments, the at least one solvent is a natural solvent.

Aptly, the solvent is a by-product of biofuel production.

Aptly, the solvent comprises solketal (Augeo® SL 191). Aptly, the solvent has a low evaporation rate allowing for a sustained release of the valerian oil and one or more further essential oils over a prolonged time, such as, for example between about 1 and 10 hours. Aptly, the solvent has a low evaporation rate allowing for a sustained release of the valerian oil and one or more further essential oils over a prolonged time between about 2 and 6 hours.

In certain embodiments, the composition comprises the at least one preservative in an amount of between about 0.05% and 1% v/v, for example between about 0.1 and 0.5% v/v. In certain embodiments, the composition comprises the at least one preservative in an amount of between about 0.1 and 0.3% v/v, e.g. about 0.2% v/v.

In certain embodiments, the at least one preservative comprises a formaldehyde releaser. Aptly, the formaldehyde releaser is hydantoin DMDM.

In certain embodiments, the composition comprises the at least one pH stabiliser in an amount of between about 0.005% to about 0.06% v/v. Aptly, the composition comprises the at least one pH stabiliser in an amount of between about 0.01 to about 0.05% v/v. Aptly, the composition comprises the at least one pH stabiliser in an amount of between about 0.02 to about 0.04% v/v. For example, in one embodiment, the composition comprises the at least one pH stabiliser in an amount of about 0.03% v/v of the composition.

In certain embodiments, the at least one pH stabiliser comprises a base. In certain embodiments, the at least one pH stabiliser comprises an alkali. In certain embodiments, the at least one stabiliser is sodium hydroxide.

In certain embodiments, the composition has a stable pH value. For example, the composition typically has a stable pH value in the range of about 6.0 to about 7.5.

In certain embodiments, the composition has a neutral pH value.

In certain embodiments, the composition has a pH value of 7.

In certain embodiments, the base e.g. sodium hydroxide aids neutralisation of the acids in the Valerian oil which prevents any changes in pH occurring in the composition over an extended period of time (e.g. more than one year, e.g. two or more years e.g. up to 3 years from manufacture).

In certain embodiments, the composition comprises more than one pH stabilisers. In certain embodiments, the composition comprises EDTA. In certain embodiments, the composition comprises the EDTA in an amount of between about 0.05% to about 0.3% v/v. Aptly, the composition comprises EDTA in an amount of between about 0.08 to about 0.14% v/v. For example, in one embodiment, the composition comprises EDTA in an amount of about 0.1% v/v of the composition.

In certain embodiments, the EDTA is EDTA.Na4 (ethylene diamine tetraacetic acid tetrasodium). Aptly, the composition comprises EDTA.Na4 in an amount of between about 0.05% to about 0.3% v/v. Aptly, the composition comprises EDTA.Na4 in an amount of between about 0.08% to about 0.14% v/v. For example, in one embodiment, the composition comprises EDTA.Na4 in an amount of about 0.1% v/v of the composition.

In certain embodiments, the composition comprises sodium hydroxide in an amount of between about 0.01% to about 0.05% v/v and EDTA in an amount of between about 0.05% to about 0.3% v/v. Through numerous trials, the inventors have unexpectedly shown that such a combination stabilises the pH of compositions of the invention over an extended period of time.

In addition, the inventors have unexpectedly shown that the blend of valerian oil and/or one or more further essential oils may exhibit a synergistic effect in providing a natural or primarily natural composition that is able to mimic GABA.

In a preferred embodiment, the composition of the invention therefore comprises:
a.) valerian oil in an amount of between about 0.1 to 0.5% v/v of the composition;
b.) further essential oils comprising vetiver oil, basil oil and clary sage oil in an amount of between about 0.05% to 1% v/v each of the composition;
c.) water;
d.) at least one preservative;
e.) at least one solvent;
f.) pH stabilisers comprising sodium hydroxide in an amount of between 0.01 to about 0.05% v/v and EDTA in an amount of between 0.05% to about 0.3% v/v; and
g.) at least one emulsifier.

In certain embodiments, the composition is a natural composition.

In certain embodiments, the composition is environmentally friendly. Aptly, the composition comprises at least about 90% v/v components that are derived from renewable and/or recycled sources. Aptly, the composition does not exhibit adverse effects to an ecological system and/or the environment during production. Aptly, the composition does not exhibit adverse effects to an ecological system and/or the environment during use. Aptly, the composition does not exhibit adverse effects to an ecological system and/or the environment during disposal.

In certain embodiments, the composition is in the form of an oil-in-water composition.

In certain embodiments, the composition comprises valerian oil and water in a ratio of between about 1:98 to about 1:980. In certain embodiments, the composition comprises valerian oil and water in a ratio of between about 1:200 to about 1:500. In certain embodiments, the composition comprises valerian oil and water in a ratio of between about 1:300 to about 1:400. In certain embodiments, the composition comprises valerian oil and water in a ratio of between about 1:320 to about 1:350. In certain embodiments, the composition comprises valerian oil and water in a ratio of about 1:331.

In certain embodiments, the composition comprises valerian oil and one or more further essential oils in a ratio of between about 1 (valerian):0.01 (total amount of further essential oils) to about 1 (valerian):10 (total amount of further essential oils). In certain embodiments, the composition comprises a ratio of valerian oil to total amount of the one or more further essential oils in a range of about 1:1 to about 1:5. For example, in one embodiment, the composition comprises valerian oil and one or more further essential oils in a ratio of about 1:1 to about 1:2. For example, in one embodiment, the composition comprises valerian oil and the total amount of one or more further essential oils in a ratio about 1:1.5.

In certain embodiments, the composition comprises valerian oil and emulsifier in a ratio in a range of between about 1 (valerian oil):1 (emulsifier) to about 1:90. In certain embodiments, the composition comprises valerian oil and emulsifier in a ratio of about 1:5 to about 1:50, e.g. of about 1:10 to about 1:20. For example in certain embodiments, the composition comprises valerian oil and emulsifier in a ratio of about 1:18.5.

In certain embodiments, the composition comprises valerian oil and solvent in a ratio of between about 1 (valerian oil):1 (solvent) to about 1:90 of valerian oil to solvent. In certain embodiments, the composition comprises valerian oil and solvent in a ratio of about 1:5 to about 1:50, for example range of about 1:10 to about 1:20. For example, in one, embodiment, the composition comprises valerian oil and a preservative in a ratio of about 1:18.5.

In certain embodiments, the composition comprises valerian oil and a preservative in a ratio of between about 1 (valerian):0.05 (preservative) to about 1:10. Aptly, a range of about 1:0.1 to about 1:5. Aptly, a range of about 1:0.5 to about 1:2. Aptly, a range of about 1:0.6 to about 1:0.6. For example, in one embodiment, the composition comprises valerian oil and a preservative in a ratio of about 1:0.75.

In certain embodiments, the composition comprises valerian oil and at least one pH stabiliser in a ratio of between about 1 (valerian):0.005 (pH stabiliser) to about 1:3. For example, in one embodiment, the composition comprises valerian oil and at least one pH stabiliser in a ratio of 1:0.111.

In certain embodiments, the composition comprises valerian oil and EDTA in a ratio of between about 1 (valerian):0.05 (EDTA) to about 1:15. Aptly, the composition comprises valerian oil and EDTA in a ratio of between about 1:0.1 to about 1:5. For example, in one embodiment, the composition comprises valerian oil and EDTA in a ratio of about 1:0.37.

In certain embodiments, the composition essentially consists of:
a.) 5% v/v solvent;
b.) 5% v/v surfactant;
c.) 0.2% v/v preservative;
d.) 0.27% v/v valerian oil;
e.) 0.2% v/v vetiver essential oil;
f.) 0.1% v/v basil essential oil;
g.) 0.1% v/v clary sage essential oil;
h.) 0.1% v/v EDTA;
i.) 0.03% v/v pH stabiliser; and
j.) 89.00% v/v water.

In certain embodiments, the composition essentially consists of:
a.) 5% v/v Augeo® SL 191;
b.) 5% v/v Surfacare T20 (006);
c.) 0.2% v/v Hydantion DMDM (0.3%);
d.) 0.27% v/v valerian oil;
e.) 0.2% v/v vetiver essential oil;
f.) 0.1% v/v basil essential oil;
g.) 0.1% v/v clary sage essential oil;
h.) 0.1% v/v EDTA;
i.) 0.03% v/v sodium hydroxide; and
j.) 89.00% v/v water.

In certain embodiments, the composition is for reducing the symptoms of stress of a bird.

In certain embodiments, the composition is for reducing the symptoms of stress of a mammal. Aptly, the mammal is a dog. Aptly, the mammal is a human. Aptly, the mammal is a cat. Aptly, the mammal is a rabbit.

In certain embodiments, the composition is for reducing the symptoms of stress of a reptile.

In certain embodiments, the composition is for delivery to a volume of air.

In certain embodiments, the composition is for delivery to a surface.

According to a second aspect of the present invention there is provided, a kit comprising a composition as described herein and at least one delivery element for delivering the composition to an environment.

In certain embodiments, the at least one delivery element comprises an atomiser.

In certain embodiments, the atomiser comprises an electrically operated pump and spray mechanism. Aptly, the atomiser comprises a portable electrical power supply. Aptly, the portable electric power supply is at least one battery. Aptly, the electrically operated pump and spray mechanism are configured to be operated automatically, that is to say not by a user. Aptly, the pump and spray mechanism are configured to be operated automatically at a time interval. Aptly, the time interval is at least 2 minutes. Aptly, the time interval is 15 minutes. Aptly, the time interval is 30 minutes.

In certain embodiments, the atomiser comprises a manually operated pump and spray mechanism. That is to say, the mechanism is directly operated by a user to deliver the composition to an environment.

In certain embodiments, the delivery element comprises at least one material element impregnated with the composition. Aptly, the material element is a woven or non-woven fabric material. Aptly, the material element is provided in a sealed (i.e. liquid and/or air tight) container such as a sachet, bag, envelope or pouch.

In certain embodiments, the composition is for delivery to a volume of air.

In certain embodiments, the composition is for delivery to a surface.

Certain embodiments of the present invention may help with increasing attentiveness and responsiveness of an animal or human.

Certain embodiments of the present invention may reduce stress and anxiety within a relatively short period of time after delivering the composition.

Certain embodiments of the present invention may help to reduce aggression due to stress and anxiety in an animal or human.

Certain embodiments may help with training an animal.

Certain embodiments of the present invention may maintain a neutral pH in storage or when in use.

DETAILED DESCRIPTION OF CERTAIN EMBODIMENTS

Certain embodiments of the present invention will now be described hereinafter, by way of example only, with reference to the accompanying drawings in which.

Figure 1:
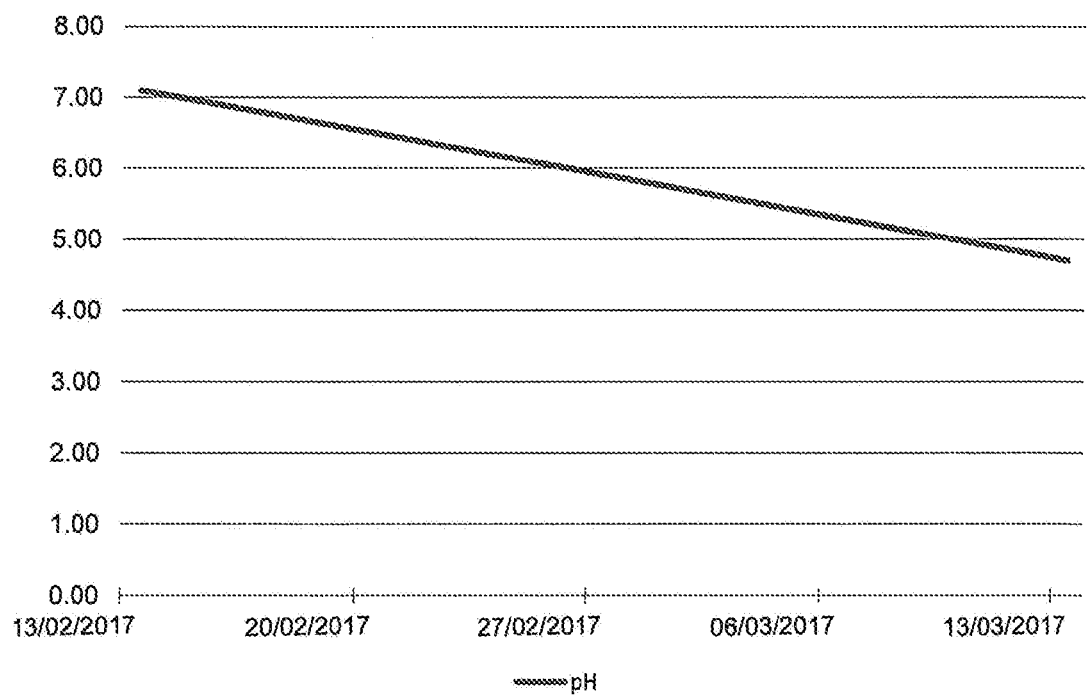
FIG. 1 shows the results of a first trial of triethanolamine (TEA) on the pH stability of a composition of the invention over time.

According to a first aspect of the present invention there is provided, a composition for reducing the symptoms of stress of an animal or human, the composition comprising:
a.) valerian oil;
b.) one or more further essential oils
c.) water
d.) at least one preservative
e.) at least one solvent
f.) at least one pH stabiliser; and
g.) at least one emulsifier.

In certain embodiments, the composition comprises valerian oil in an amount of between about 0.01% to about 1% volume per volume (v/v) of the composition. Aptly, the composition comprises valerian oil in an amount of between about 0.05% to about 0.5% v/v of the composition. Aptly, the composition comprises valerian oil in an amount of between about 0.1% to about 0.3% v/v of the composition. For example, in one embodiment, the composition comprises valerian oil in an amount of about 0.27% v/v of the composition. In another embodiment, the composition comprises valerian oil in an amount of about 0.1% v/v of the composition.

In certain embodiments, the valerian oil is obtained by a cold extraction process. As used herein the term "cold extraction" refers to a process of extracting that does use elevated temperatures (as is used in processes such as steam distillation). For example, the valerian oil may be obtained by cold press extraction. Without being bound by theory cold extraction processes may reduce the degradation of naturally occurring compounds found within a valerian root that the oil may be extracted from.

In certain embodiments, the one or more further essential oils comprises one or more of vetiver and/or basil and/or sage. Aptly, the one or more essential oils is a mixture of vetiver, basil and sage. In certain embodiments, the one or more further essential oils provide an aroma to the composition as well as enhancing the calming and destressing effects of the composition. Aptly, the sage oil is clary sage oil.

Clary sage oil may have the advantage of having a different or less odorous odour than sage oil. In certain embodiments, use of clary sage oil may help to reduce side effects, such as but not limited to sternutation (sneezing), epiphora and pruritus. In certain embodiments, clary sage oil may decrease discomfort, which may lead to increased stress and/or anxiety, the composition may cause in an animal or human due to malodourous smell and/or adverse side effects.

In certain embodiments, the composition comprises the at least one emulsifier in an amount of between about 1% and 9% v/v of the composition. Aptly, the composition comprises the at least one emulsifier in an amount of between about 2% v/v and 7% v/v, e.g. between about 4% and 6% v/v. For example, in one embodiment, the composition comprises the at least one emulsifier in an amount of about 5% v/v of the composition.

The emulsifier may be any suitable emulsifier. As used herein the term "emulsifier" refers to a substance that can stabilise a mixture of two or more immiscible liquids so as to form an emulsion. As used herein the term "emulsion" refers to a mixture of two or more substances wherein both the dispersed and continuous phase are liquid.

In certain embodiments, the at least one emulsifier comprises at least one surfactant. Aptly, the at least one surfactant comprises at least one ethoxylated sorbitan ester. Aptly, the at least one ethoxylated sorbitan ester comprises polyoxyethelyene sorbitan monolaurate.

In certain embodiments, the composition comprises the at least one solvent in an amount of between about 1% and 9% v/v of the composition. Aptly, the composition comprises the at least one solvent in an amount of between about 3% to 7% v/v of the composition. Aptly, the composition comprises the at least one solvent in an amount of between about 4% and 6% v/v of the composition. For example, in one embodiment, the composition comprises the at least one solvent in an amount of 5% v/v.

As used herein the term "solvent" refers to a compound or composition comprising at least one volatile substance that is able to act as vehicle for other compounds such as at least one of the valerian oil and/or the one or more further essential oils. Aptly, the solvent is vaporised by evaporation.

In certain embodiments, the at least on solvent comprises a low odour solvent. The term "low odour" as used herein refers to a substance that has a low concentration of volatile substances that are perceived or sensed by the olfactory sensory system of an animal or human. In certain embodiments, the low odour solvent is a glycerine based solvent. Glycerine based solvents may be produced from renewable sources and so may be less damaging to the environment.

In certain embodiments, the at least one solvent is a natural solvent. As used herein the term "natural" refers to solvents that are animal, plant or mineral in origin, including solvents that are refined from natural substances or otherwise treated to remove synthetic contaminants. The term "synthetic" as applied to solvents refers to solvents that are chemically synthesized by humans from non-solvent starting materials.

Aptly, the solvent is a by-product of biofuel production.

Without being bound by theory natural solvents may have fewer adverse side effects on an animal or human and be more environmentally friendly.

Aptly, the solvent comprises solketal (Augeo® SL 191). Aptly, the solvent has a low evaporation rate allowing for a sustained release of the valerian oil and the one or more further essential oils over a prolonged time, such as, for example between about 1 and 10 hours. Aptly, the solvent has a low evaporation rate allowing for a sustained release of the valerian oil and the one or more further essential oils between about 2 and 6 hours.

In certain embodiments, use of a low odour solvent may help to reduce side effects, such as but not limited to sternutation (sneezing), epiphora and pruritus. In certain embodiments, a low odour solvent may decrease discomfort, which may lead to increased stress and/or anxiety, the composition may cause in an animal or human due to malodourous smell and/or adverse side effects.

As used herein the terms "volatile" and "volatility" refer to the tendency of a substance to vaporise.

As used herein the terms "vaporise" and "vaporisation" refer to the transition of a substance from the liquid phase to the gas phase. Vaporisation can occur by two main processes: evaporation or boiling.

As used herein the term "evaporation rate" refers to the volume of a substance that transitions from the fluid phase to the gas phase over a period of time, when exposed to temperatures below the boiling temperature of the substance.

In certain embodiments, the composition comprises the at least one preservative in an amount of between about 0.05% and 1% v/v, for example between about 0.1 and 0.5% v/v. In certain embodiments, the composition comprises the at least one preservative in an amount of between about 0.1 and 0.3% v/v, e.g. about 0.2% v/v.

As used herein the term "preservative" refers to a compound that can help prevent or delay microbial and/or chemical degradation of a composition and compounds thereof. Any suitable preservative may be used.

In certain embodiments, the at least one preservative comprises a formaldehyde releaser. As used herein the term "formaldehyde releaser" refers to a chemical that releases formaldehyde into an environment. Aptly, the formaldehyde releaser is hydantoin DMDM.

In certain embodiments, the composition comprises the at least one pH stabiliser in an amount of between about 0.005% to about 0.06% v/v. Aptly, the composition comprises the at least one pH stabiliser in an amount of between about 0.01 to about 0.05% v/v. Aptly, the composition comprises the at least one pH stabiliser in an amount of between about 0.02 to about 0.04% v/v. For example, in one embodiment, the composition comprises the at least one pH stabiliser in a concentration of about 0.03% v/v of the composition.

In certain embodiments, the at least one pH stabiliser comprises a base. In certain embodiments, the at least one pH stabiliser comprises an alkali. In certain embodiments, the at least one stabiliser is sodium hydroxide. As used herein the term "pH stabiliser" refers to a compound that can help prevent or reduce changes in the pH value of a composition.

The use of a pH stabiliser may help maintain a pH value of the composition. Aptly, the pH stabiliser maintains a pH value in a range of 6 to 8. Aptly, the at least one pH stabiliser maintains a pH value of 7. Aptly, the at least one pH stabiliser maintains a neutral pH. A neutral pH may provide a more stable composition and longer shelf life as well as being safe to apply directly to skin and coat of an animal.

In certain embodiments, the composition comprises at least two pH stabilisers. In certain embodiments, the composition comprises EDTA.

The inventor's research and trials have shown that valerenic acid content in valerian oil has a direct and adverse effect on the pH value, stability and shelf life of the compositions of the invention. Through numerous trials, the inventors have unexpectedly shown that a composition comprising at least two pH stabilisers e.g. EDTA and sodium hydroxide performs better than traditional stabilisers such as triethanolamine and stabilises the composition for up to 3 years. In preferred embodiments, the invention therefore provides a composition comprises sodium hydroxide in an amount of between about 0.01% to about 0.05% v/v and EDTA in an amount of between about 0.05% to about 0.3% v/v.

In certain embodiments, the composition is a natural composition. As used herein the term "natural composition" refers to a composition that comprises at least about 90% v/v natural components. Aptly, a natural composition comprises at least about 91% v/v, at least about 92% v/v, at least about 93% v/v, at least about 94% v/v, at least about 95% v/v, at least about 96% v/v, at least about 97% v/v, at least about 98% v/v, at least about 99% v/v, at least about 100% v/v natural components. As used herein the term "natural" refers to components that are animal, plant or mineral in origin, including components that are refined from natural substances or otherwise treated to remove synthetic contaminants. The term "synthetic" as used herein refers to components that are chemically synthesized by humans.

In certain embodiments, the composition is environmentally friendly. As used herein the terms "environmentally friendly" and "eco-friendly" are interchangeable and refer to compositions that comprise at least about 80% v/v components that are derived from renewable and/or recycled sources and/or do not exhibit adverse effects to ecological systems and/or the environment during production, use and/or disposal thereof. Aptly, an environmentally friendly composition comprises at least about 85% v/v, at least about 90% v/v, at least about 95% v/v, at least about 100% v/v, derived from renewable and/or recycled sources.

Without being bound by theory, natural compositions may be less damaging to or have reduced adverse effects on an environment when in use and/or disposed of. This may allow for certain embodiments of the compositions disclosed herein to be used and/or disposed of in a simple and/or inexpensive manner without having adverse effects on the environment, for example without having adverse effects on water systems such as rivers if, for example, disposed of via a drainage system, or in a landfill site. The use of renewable and/or recycled components may help reduce the carbon footprint used to manufacture certain embodiments of the compositions disclosed herein.

In certain embodiments, the composition is in the form of an oil-in-water composition.

Certain embodiments of the compositions disclosed herein are for use in reducing the symptoms of stress and/or anxiety in animals.

Animals may not show external symptoms of stress or in some situations stress or anxiety can manifest in the animal as for example, destructive behaviour (such as chewing furniture), increased vocalisation (such as barking, whining or howling), self-harming behaviour (such as over-grooming, chewing of paws and increased itching and scratching of the skin or fur) and changes in physical behaviour or character (such as excessive panting, self-isolation, aggression, decreased attentiveness, decreased obedience and/or decreased responsiveness). Stress can also manifest itself as symptoms such as lethargy and depression both in humans and animals.

Stress in an animal may also be detected by the displaying of calming signals by the animal. As used herein the term "calming signals" refers to the use of body language by an animal to indicate and/or communicate that a situation is uncomfortable or causing stress. For example, in dogs calming signals may include but are not limited to averting eyes, bowing, licking of the nose, yawning, sniffing, laying down, turning away and/or increased blinking.

Symptoms of stress and how they manifest may vary between different animals and individuals and may also include but are not limited to one or more of: muscle pain; increased heat rate; increased hair loss; decrease of appetite; insomnia; increased perspiration; headaches; shortness of breath; and/or decreased concentration levels.

The causes of stress in an animal or human may also vary for species and individuals. For example, for household pets such as dogs, stress and its symptoms may be caused due to prolonged periods of separation, present or past ill treatment or abuse, changes in living environment (for example changes in routine, changes in living arrangements, changes in carers or introduction of other animals into a home), confinement, social interactions, grooming, interactions with veterinarians, lack of mental stimulation (such as a lack of training, exercise and/or play) and loud noises. Other causes of stress will be known by those skilled in the art.

Certain embodiments of the present invention may be in a liquid form. In certain embodiments, the composition is delivered to an environment by an atomiser. An atomiser may be any apparatus suitable for dispersing a liquid into a spray. As used herein the term "spray" refers to a dynamic dispersion of liquid droplets in a gas. For example, certain embodiments of the present invention may be passed from a reservoir containing the composition by a pumping mechanism through a passageway wherein the composition is acted upon by a force causing the composition to be atomised (dispersed) into droplets. Dispersion may be achieved by a mechanical force such as by using a spray nozzle. Examples of suitable spray nozzles may include but are not limited to plain orifice nozzles, shaped orifice nozzles, surface impingement nozzles and compound nozzles. Other suitable atomisation methods and apparatus will be known by those skilled in the art.

Atomisation of certain embodiments of the present invention may increase the surface area of a composition and may help to deliver a composition over a greater area or volume.

In certain embodiments, the atomiser may include an electrically operated pump and spray mechanism. Such atomisers may include a portable electrical power supply such as batteries. In certain embodiments, the atomisers may be powered by mains electricity. The automatic operation of the pump and spray mechanism allows for certain embodiments of compositions of the present invention to be delivered to an environment when a user is not in the immediate vicinity of the atomiser and without requiring a user to actively operate the atomiser, for example if a dog is left in a house without an owner and/or carer then the electrically operated atomiser can deliver certain embodiments of the compositions of the present invention automatically. The electrically operated pump and spray mechanism may be temporally controlled and so may be used to deliver a composition at predetermined time intervals.

In certain embodiments, the pump and spray mechanism may be operated manually, for example the pump and spray mechanism may include a handle element that is depressed by a user causing the atomiser to deliver a composition as a spray.

In certain embodiments, the composition may be delivered to an environment by a material element such as a cloth that has been impregnated with compositions of certain embodiments of the present invention. Impregnation may be achieved by soaking or saturating a material with a composition of certain embodiments of the present invention. In certain embodiments, wherein a cloth has been impregnated with certain embodiments of the compositions of the present invention, the composition may be delivered by contacting the cloth to a surface and transferring at least a portion of the composition from the cloth to the surface. In certain embodiments, the impregnated cloth may be provided to a user within an air and/or liquid tight container such as a sachet or envelope. Providing the impregnated cloth within an air and/or liquid tight container helps prevent evaporation of the composition prior to unsealing of the sachet or envelope, therefore extending the useable lifetime of the impregnated cloth.

Certain embodiments of the present invention may be delivered to a surface the animal will be or is in close proximity to, for example the surface of a bed, mat, area of floor or table where the animal may be and/or will be located. In certain embodiments, the composition may be delivered to a surface and then subsequently transferred to a surface of an animal. For example, certain embodiments of the compositions may be delivered to a tissue, cloth or the hands of an owner or carer and then transferred to the chest and/or muzzle of an animal such as a dog. In certain embodiments, the composition may be directly applied to a surface of the animal or human. In certain embodiments, the composition may be applied to one or more articles of attire of an animal such as a collar, coat or bandana or other suitable animal attire which is then secured to the animal. In certain embodiments, compositions may be delivered to the surface of one or more articles of attire of an owner or carer. For example, if training an animal such as a dog, certain embodiments of the composition may be delivered to the surface of an owners clothing that is in close proximity to the dog so that the dog remains attentive and responsive when encountering potentially stressful situations when walking close to the owner or carer such as when on a lead. Certain embodiments of the present invention may exhibit calming effects and reduction of symptoms of stress in a relatively short period of time. For example, within minutes of delivery of certain embodiments of the present invention to an environment.

Once delivered to an environment such as a surface, in certain embodiments, the solvent evaporates and vaporises at least a portion the valerian oil and/or one or more further essential oils into the air surrounding the surface the composition has been delivered to. The evaporated components such as the valerian oil and one or more further essential oils are then inhaled by an animal. In certain embodiments, wherein the composition is delivered by an atomiser the composition may be directly inhaled by an animal from the air. In certain embodiments, the solvent is a low odour solvent. Low odour solvents may help reduce any discomfort certain embodiments of the compositions may cause for animals with a sensitive olfactory system, such as dogs. Without being bound by theory, the use of at least one pH stabiliser helps reduce adverse side effects, such as itching, sneezing, coughing or irritation of the skin, in an animal or human when or if the composition is inhaled or is applied directly to the surface of an animal or human.

In certain embodiments, the solvent has a low evaporation rate which may help in extending the period of time that certain embodiments of the present invention may help to reduce the symptoms of stress. In certain embodiments, the solvent is a natural solvent. Natural solvents may help reduce damaging effects to the environment and/or reduce adverse side effects in a target animal or human.

In certain embodiments, wherein the composition is delivered as a spray, the solvent may help to solubilise the valerian oil and/or one or more essential oils into the water. Without being bound by theory the solvent may allow for a fine spray (having a substantially small average droplet size). Without being bound by theory the use of a solvent may help reduce the viscosity of a composition. Reduced viscosity may help to allow a higher flow rate of the composition when sprayed allowing for greater dispersion of the composition to occur. Solvents may also help reduce the surface tension of a composition. Reduced surface tension may help stabilise small droplets, thus providing and maintaining a fine spray. A fine spray may have a high total surface area and therefore may increase the volume of the composition inhaled by an animal or human target. A fine spray and high total surface area may also help increase the speed of evaporation of the solvent and therefore increase the speed and volume of release of the valerian oil and/or one or more essential oils to the surrounding environment. Increased speed of evaporation may decrease the time taken for certain embodiments of the compositions described herein to reduce stress and calm an animal or human target. A fine spray may also help improve efficiency of the calming and/or destressing effect certain embodiments may have on an animal or human target.

In certain embodiments, the solvent is evaporated into the environment and may be inhaled by an animal or human. Many synthetic solvents are known to cause damage to the environment and/or may also cause irritation or adverse side effects in animal or human targets. Thus, the use of a natural solvent in certain embodiments of the compositions as described herein may help reduce damaging effects to the environment as well as reducing adverse side effects, while also allowing optimal delivery of the valerian oil and one or more further essential oils.

Without being bound by theory the valerian oil and/or valerian oil and further essential oils may mimic the molecule gamma-Aminobutyric acid (GABA). GABA is an inhibitory neurotransmitter that may help reduce neuronal excitability throughout the nervous system. By mimicking the effects of GABA certain embodiments of the present invention may help to reduce neuronal excitement in an animal and therefore may have a calming effect on an animal, therefore helping reduce the symptoms of stress and/or anxiety.

Without being bound by theory, in certain embodiments, the mixture of components of certain embodiments of the compositions as described herein may exhibit a synergistic effect in providing a natural or primarily natural composition that is able to mimic GABA. Aptly, the blend of valerian oil and/or one or more further essential oils exhibit a synergistic effect in providing a natural or primarily natural composition that may be able to mimic GABA.

Certain embodiments of the present invention may help reduce neuronal excitability and make the animal more responsive and/or attentive. This may help a carer such as an owner, vet or trainer to work on dealing with issues which may cause stress and/or anxiety and/or train the animal to be more confident and so not to have an adverse reaction and/or display symptoms of stress and/or anxiety due to causes of stress and/or anxiety.

Without being bound by theory the low percentage volume of valerian oil used in certain embodiments, may help calm an animal and reduce the symptoms of stress without sedating the animal thus helping maintain the animal in a responsive and attentive manner. As used herein the term "sedating" refers the calming of an animal or human wherein the animal or human may become lethargic, may exhibit decreased responsiveness, may exhibit a decrease in attentiveness and may cause the animal to sleep.

Example 1—Dog Grooming Salon Study

Throughout this example a composition comprising the following percentage of volume of components was used:

| | |
|---|---|
| 3-6% | Augeo ® SL 191 |
| 3-6% | Surfacare T20 (006) |
| 0.1-0.3% | Hydantion DMDM (0.3%) |
| 0.25-0.30% | Valerian Oil |
| 0.1-0.3% | Vetiver essential oil |
| 0.05-0.15% | Basil essential oil |
| 0.05-0.15% | Clary Sage essential oil |
| Remaining % Water | |

The composition as described above was applied to the grooming overalls, grooming table and waiting area of 70 different dog groomers. Groomers were then asked to assess the symptoms of stress for dogs being groomed in comparison to the dogs previous grooming visits and record and report these assessments in a questionnaire. The following definitions we provided to groomers to help them with their assessments:

Confident, friendly and relaxed: This is a tactile dog who will actively seek attention, enjoy being touched, tail will be wagging, will enjoy the grooming session and have a friendly disposition throughout. There should be no concerns about aggression. The dog should show no signs of any anxiety or calming signals and may even doze on the table.

Relaxed but slightly reserved: This dog may be quiet at first but friendly once settled in the environment and enjoy the attention of the grooming session. May be slightly uncomfortable around some equipment such as the dryer but return to normal is quick.

Mildly anxious, uncomfortable and fidgety: This dog may show mild avoidance, some panting, display other symptoms of stress, display calming signals and need to be coached on to the grooming table. May be uncomfortable around some equipment such as the dryer. Will be alert throughout.

Nervous, displaying calming signals: calming signals are displayed by a dog who is feeling anxious and is trying to diffuse a tense situation. Some behaviours can be quite subtle and easily missed. They include lip licking, avoidance such as a head turn, turning body away, yawning, lifting a paw, sniffing the ground and shaking off.

Very anxious: This dog may be panting, shaking, showing other symptoms of stress, displaying calming signals, may be withdrawn, tail may be tucked under and may resort to growling, snarling and biting. Dog may already be or need to be muzzled. This dog may also display learned helplessness.

Learned helplessness: When there is no possibility of a dog avoiding an aversive stimulus, a state of becoming resigned to unpleasantness may occur and this is termed 'learned helplessness'. When given an opportunity to escape or avoid an aversive situation, the dog will remain where it is as if it has given up.

Of the 70 groomers 96% said they would recommend the composition for use in reducing symptoms of stress in dogs.

Of 242 dogs assessed 80% were reported to have significantly or moderately improved behaviour when the composition was applied to the environment as compared to previous visits when the composition was not used.

61% of dogs recorded as previously displaying symptoms of stress when having their nails clipped showed a decrease in the symptoms of stress when the composition was used.

59% of dogs previously recorded as showing symptoms of stress when having their fur cut or clipped showed decreased symptoms of stress when the composition was used.

Example 2—pH Stabilisation and Shelf Life Trials of Pet Remedy Formulations

The compositions of the invention are water based and preferably contain a special blend of valerian oil with vetiver, basil and clary sage essential oils.

The acids present in the valerian oil have an adverse effect on the pH value and therefore stability, and shelf life of the formulation.

Numerous trials and developments were undertaken to stabilise the pH value of the compositions when stored and used over a period of time.

Throughout this example, a pet remedy formulation comprising the following percentage of volume of components was used (w/w %):
Valerian oil: 0.1%
Vetiver essential oil: 0.12%
Basil essential oil: 0.06%
Clary sage essential oil: 0.06%

Mixture of these oils is solubilised in a solvent enhanced with a non-ionic surfactant.

Our research and trials show vetiver, basil, and clary sage essential oils to be stable and not to have an effect on the pH value of the formulation. However, valerenic acid content in the valerian oil has a direct and adverse effect on the pH value, stability, and shelf life of the composition. It is essential that pet products have a stable pH in the range of 6.0-7.5.

1. Valerian Absolute Oil: (CAS No. 8008-88-6)

Key Constituents

The three sesquiterpenes, valerenic acid and its hydroxy and acetoxy derivatives, are the primary characteristic markers of *Valeriana Officinalis*.

Valerenic acid, 3-methylvaleric acid, isovaleric acid and salts of iso-valeric acid (e.g; ammonium, sodium, and Zinc) are listed as synthetic flavouring substances permitted for direct addition to food. [21CFR172.515] (U.S. FDA.2009c.)

2. Vetiver Essential Oil (CAS No. 8016-96-4)
3. Basil Essential Oil (CAS No. 84775-71-3)
4. Clary Sage Essential Oil (CAS No. 8016-63-5)

Improved Pet Remedy Formulations

Valerian Absolute Oil is the only oil in the Pet Remedy formulation with an unstable molecular structure. This is because of its free acid groups. Neutralisation of these acid groups can be achieved by saponification.

Various ingredients were trialled for neutralisation as explained below:

Trial 1

Triethanolamine (0.063%) added to batch was not a stable neutralisation. Shelf-life was not maintained. pH showed to be unstable within short period.

Trial 2

EDTA.Na4 (0.3%) added by a different method showed an increased shelf life; However, a drop in pH value in accelerated tests was still observed.

Trial 3

NaOH (0.03%) With an alteration to method of manufacture neutralising valerian oil with 0.13% EDTA.Na4 absolute oil with sodium hydroxide separately and adding its saponified form to bulk resulted in required pH stabilisation.

Calculation Followed for Amount of Sodium Hydroxide (NaOH) Required:

A molecular weight of 234.33 of Valerian absolute oil, requires a calculated amount of sodium hydroxide that would be equivalent to 0.0461 g of Sodium Hydroxide (solid) for the acid present in the Valerian absolute, for neutralization.

Neutralisation with Sodium hydroxide is also a safe option:

Its salt formation mentioned above has been acceptable for direct addition to food by the FDA.

The formulation contains 0.1% Valerian absolute; which requires a neutralisation to ratio 1:3

The target is to maintain the pH value in the range (6.0-7.5)

Stability Results for the 3 Trials Undertaken:

In all trials the same batches of oils were used to ensure consistency.

All the trials are based on an Initial formulation release specification of pH: 7.5

Note Temperature Affects pH Values.

Neutral pH for pure water at 50 degrees C. is calculated to be: 6.92

Neutral pH for pure water at 0 degrees C. is calculated to be: 7.48

Trial 1—Using Triethanolamine (0.063%)

When using triethanolamine (TEA), the solution prior to stabilisation had a pH level of between 4.5 and 5.

This original method to correct the solution was to add TEA to bring the pH level up to the required level of 6.5-7.5. The formula required adding 0.063% TEA, however this was effective for an initial 48 hours but thereafter the pH level dropped (see Table below and related FIG. 1).

|  | pH | date |
|---|---|---|
| pH at start of trial at 50 degrees C. its pH revealed: | 7.1 | 13 Feb. 2017 |
| pH to date after 2 weeks at 50 degrees C. its pH revealed | 5.9 | 27 Feb. 2017 |
| pH to date after 4 weeks at 50 degrees C. its pH revealed: | 4.7 | 13 Mar. 2017 |

It was therefore concluded the TEA was not effective enough, and the trial was terminated.

Trial 2—Using EDTA.Na4 (0.3%)

EDTA.Na4 solution (38%) was then used for correcting the batch to a pH level of 6.5-7.5 with 0.3% of EDTA which was effective but still gave a drop to between 6-6.2 over a time scale of 8 weeks.

An additional 0.1% EDTA was added to take the solution back to a pH of 7.3 and this became stable but the pH level slightly dropped again.

Figure 2:
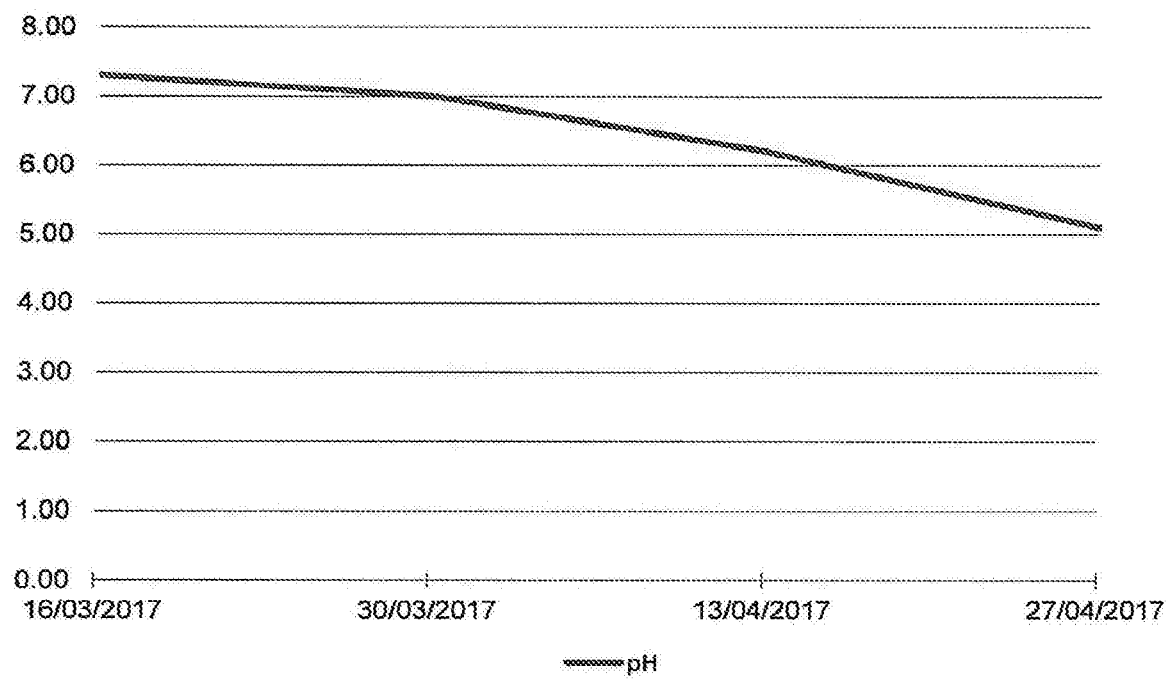
FIG. 2 shows the results of a second trial of EDTA on the pH stability of a composition of the invention over time.

After further experiments it was concluded the method of manufacture to neutralize the formula required further alteration, and a test was conducted with results shown below (and in related FIG. 2).

|  | pH | date |
|---|---|---|
| pH at start of trial at 50 degrees C. its pH revealed: | 7.3 | 16 Mar. 2017 |
| pH to date after 2 weeks at 50 degrees C. its pH revealed: | 7.0 | 30 Mar. 2017 |
| pH to date after 4 weeks at 50 degrees C. its pH revealed: | 6.2 | 13 Apr. 2017 |
| pH to date after 6 weeks at 50 degrees C. its pH revealed: | 5.1 | 27 Apr. 2017 |

The test was terminated as the formula was not stable.

Trial 3—Batch 1 Using EDTA.Na4 at 0.13% and Sodium Hydroxide at 0.03%

Findings based on 1,000 liter batches using this new method of manufacture and formula were as follows:

Batches were produced using Sodium Hydroxide and a solution of 0.2% EDTA.

Batch 1—When the Valerian Absolute was mixed with the Sodium hydroxide in a 3% pre-mix solution, the PH level was 12, and this slowly settled to 7.1 when it was introduced to the rest of the formulation solution.

Figure 3:
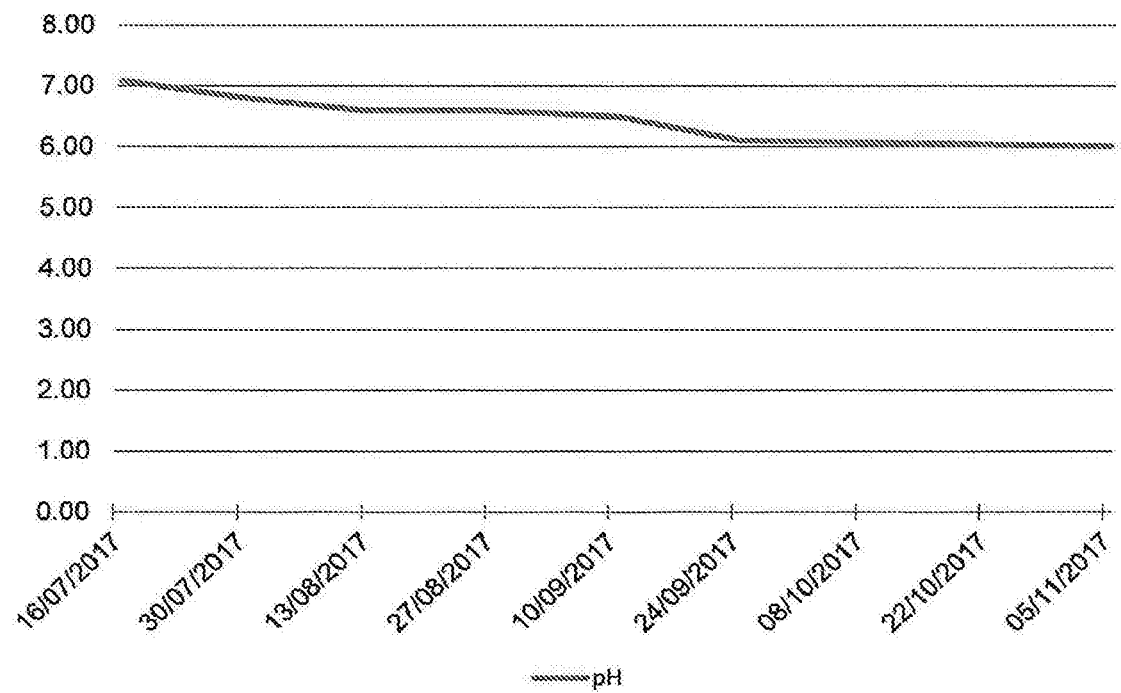
FIG. 3 shows the results of a third trial of sodium hydroxide and EDTA on the pH stability of a composition of the invention over time.

The results of Trial 3, Batch 1 are presented in the Table below (and related FIG. 3). As can be seen, the formula was stable at pH 6.0 over time.

|  | pH | date |
|---|---|---|
| pH at start of trial at 50 degrees C. its pH revealed: | 7.1 | 16 Jul. 2017 |
| pH to date after 2 weeks at 50 degrees C. its pH revealed: | 6.8 | 30 Jul. 2017 |
| pH to date after 4 weeks at 50 degrees C. its pH revealed: | 6.6 | 12 Aug. 2017 |
| pH to date after 6 weeks at 50 degrees C. its pH revealed: | 6.6 | 26 Aug. 2017 |
| pH to date after 8 weeks at 50 degrees C. its pH revealed: | 6.5 | 10 Sep. 2017 |
| pH to date after 10 weeks at 50 degrees C. its pH revealed: | 6.1 | 24 Sep. 2017 |
| pH to date after 16 weeks at 50 degrees C. its pH revealed: | 6.0 | 5 Nov. 2017 |

Trial 3—Batch 2: Accelerated Stability (50-Degree C.) and Ambient (23-Degree C.) Sample Results When the Valerian Absolute was mixed with the Sodium hydroxide in a 3% pre-mix solution the pH level was 12 this slowly settled to 6.93 when it was introduced to the rest of the formulation solution.

Figure 4:
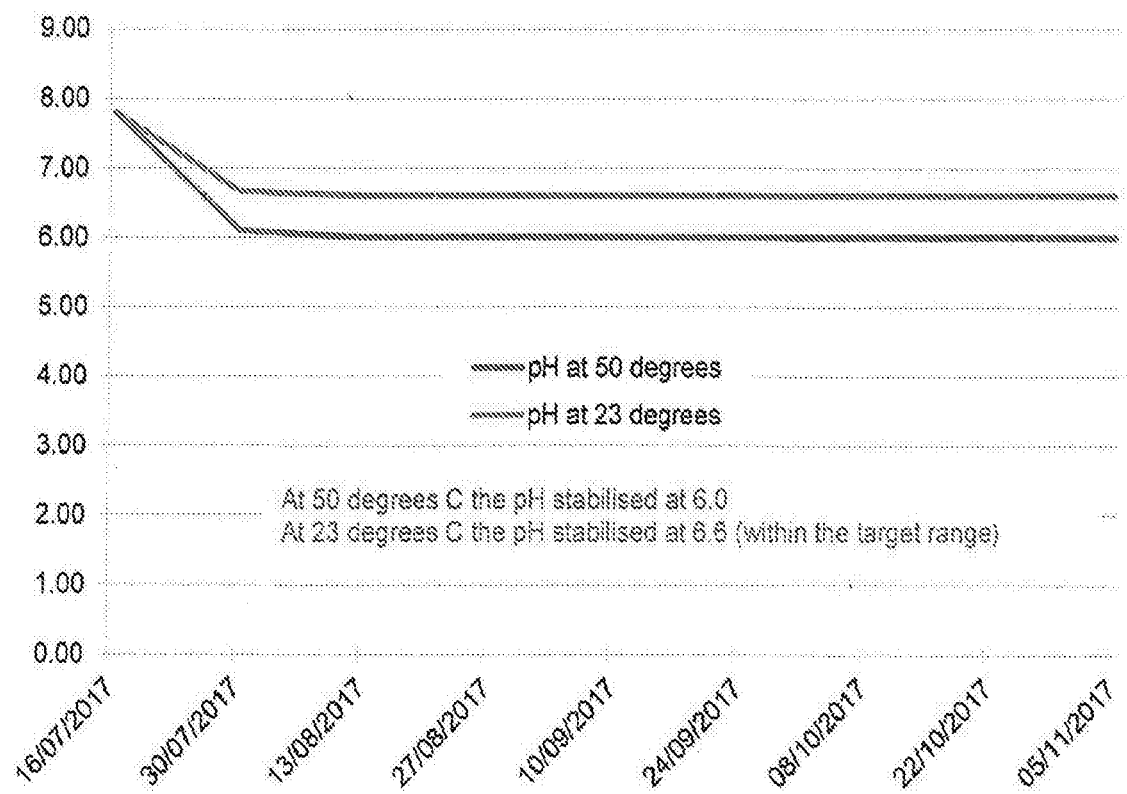
FIG. 4 shows the results of a third trial of sodium hydroxide and EDTA on the pH stability of a composition of the invention over time and at different temperatures.

As can be seen from the Table below (and related FIG. 4), at 50 degrees C. the pH stabilized at 6.0. At 23 degrees C. the pH stabilized at 6.6, also within the target range.

|  | 23 Deg C. | 50 Deg C. | date |
|---|---|---|---|
| pH at start of trial at 50 degrees C. its pH revealed: | 7.8 | 7.8 | 16 Jul. 2017 |
| pH to date after 2 weeks at 50 degrees C. its pH revealed: | 6.7 | 6.1 | 30 Jul. 2017 |
| pH to date after 4 weeks at 50 degrees C. its pH revealed: | 6.6 | 6.0 | 13 Aug. 2017 |
| pH to date after 6 weeks at 50 degrees C. its pH revealed: | 6.6 | 6.0 | 27 Aug 2017 |
| pH to date after 8 weeks at 50 degrees C. its pH revealed: | 66 | 6.0 | 10 Sep. 2017 |
| pH to date after 10 weeks at 50 degrees C. its pH revealed: | 6.6 | 6.0 | 24 Sep. 2017 |
| pH to date after 16 weeks at 50 degrees C. its pH revealed: | 6.6 | 6.0 | 5 Nov. 2017 |

Summary

The method devised above for the neutralization of valerian oil is the critical outcome of the experiments, enabling the formula to be stable, effective, and extending shelf life of the formulation to 36 months.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A composition for reducing one or more symptoms of stress of an animal or human, the composition comprising:
  valerian oil, in an amount of 0.1% to 0.3% v/v of the composition;
  one or more further essential oils;
  water in an amount of at least 80% v/v of the composition;
  at least one preservative;
  at least one solvent;
  at least one pH stabiliser; and
  at least one emulsifier,
  wherein the composition is formulated for application to skin, coat, or combinations thereof, of the animal or human.

2. The composition according to claim 1, wherein:
  the one or more further essential oils comprises one or more of vetiver oil, basil oil, clary sage oil, or combinations of any of the foregoing;

the composition comprises one or more further essentials oil in an amount of about 0.05% to about 1% v/v of the composition;

the composition comprises the at least one emulsifier in an amount of about 1% to about 9% v/v of the composition;

the composition comprises the at least one solvent in an amount of about 1% to about 9% v/v of the composition;

the composition comprises the at least one preservative in an amount of about 0.1% to about 0.5% v/v of the composition; and/or the composition comprises the at least one preservative in an amount of about 0.005% to about 0.06% v/v of the composition.

3. The composition according to claim 1, wherein:
the at least one pH stabiliser comprises sodium hydroxide in an amount of about 0.01 to about 0.05% v/v.

4. The composition according to claim 1, which comprises at least two pH stabilisers, wherein optionally the composition further comprises EDTA, optionally wherein the composition comprises EDTA in an amount of between about 0.05% to about 0.3% v/v of the composition.

5. The composition according to claim 1, comprising sodium hydroxide in an amount of between about 0.01% to about 0.05% v/v and EDTA in an amount of between about 0.05% to about 0.3% v/v, optionally wherein the composition comprises a ratio of about 1:0.37 of valerian oil to EDTA.

6. The composition according to claim 1, wherein the at least one preservative comprises a formaldehyde releaser, optionally wherein the formaldehyde releaser is hydantoin DMDM.

7. The composition according to claim 1, wherein the at least one solvent comprises at least one low odour solvent, optionally wherein the at least one low odour solvent comprises a glycerine-based solvent, optionally wherein the glycerine-based solvent is solketal.

8. The composition according to claim 1, wherein the at least one emulsifier comprises an ethoxylated sorbitan ester, optionally wherein the ethoxylated sorbitan ester comprises polyoxyethelyene sorbitan monolaurate.

9. The composition according to claim 1, wherein the composition is in the form of an oil-in-water composition.

10. The composition according to claim 1, wherein the valerian oil is obtained by a cold extraction process.

11. The composition according to claim 1, wherein the composition has a stable pH value in the range of about 6.0 to about 7.5 or wherein the composition has a neutral pH.

12. The composition according to claim 1, wherein:
the one or more further essential oils comprise vetiver oil, basil oil and clary sage oil, each independently in an amount of about 0.05% to about 1% v/v of the composition; and the at least one pH stabiliser comprises sodium hydroxide in an amount of about 0.01% to about 0.05% v/v and EDTA in an amount of about 0.05% to about 0.3% v/v of the composition.

13. The composition according to claim 1, wherein the animal is a bird, mammal or reptile.

14. A composition according to claim 1 for use in a method of reducing the symptoms of stress and/or anxiety in an animal or human.

15. A method of reducing the symptoms of stress and/or anxiety in an animal or human, comprising administering a therapeutically effective amount of a composition according to claim 1 to the skin, coat, or both the skin and the coat, of the animal or human.

16. The method according to claim 15, wherein the animal is a dog.

17. A kit comprising a composition according to claim 1 and at least one delivery element for delivering the composition to an environment.

18. A kit according to claim 17, wherein:
(i) the at least one delivery element comprises an atomiser, optionally wherein the atomiser comprises a portable electrical power supply; and/or
(ii) the at least one delivery element comprises at least one material element impregnated with the composition.

19. A spray mechanism comprising a reservoir comprising the composition according one of claim 1, wherein the spray mechanism is adapted to deliver the composition from the reservoir to an environment.

20. A spray mechanism according to claim 19, further comprising a pump, optionally wherein the pump is electrically or manually operated.

* * * * *

UNITED STATES PATENT AND TRADEMARK OFFICE
CERTIFICATE OF CORRECTION

| | | |
|---|---|---|
| PATENT NO. | : 12,168,032 B2 | Page 1 of 1 |
| APPLICATION NO. | : 16/979579 | |
| DATED | : December 17, 2024 | |
| INVENTOR(S) | : Martyn Christopher Barklett-Judge | |

It is certified that error appears in the above-identified patent and that said Letters Patent is hereby corrected as shown below:

In the Claims

Column 18, Line 66, Claim 2, please delete "one or more of" before the words "vetiver oil, basil oil, clary sage oil, or combinations of any of the foregoing;".

Signed and Sealed this
Fourth Day of March, 2025

Coke Morgan Stewart
*Acting Director of the United States Patent and Trademark Office*